US012471924B2

(12) United States Patent
Stefanov et al.

(10) Patent No.: US 12,471,924 B2
(45) Date of Patent: Nov. 18, 2025

(54) FLEXIBLE FEATURE FOR EMBOLIC IMPLANT DEPLOYMENT

(71) Applicant: DePuy Synthes Products, Inc., RAynham, MA (US)

(72) Inventors: Petrica Stefanov, Loughrea (IE); Daniel Solaun, Miami, FL (US); Francisco Ales, Miami, FL (US); Jasia Dickerson, Miami, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/685,197

(22) Filed: Mar. 2, 2022

(65) Prior Publication Data

US 2023/0277181 A1 Sep. 7, 2023

(51) Int. Cl.
*A61B 17/12* (2006.01)
*A61F 2/95* (2013.01)
*A61F 2/966* (2013.01)

(52) U.S. Cl.
CPC ........ *A61B 17/12022* (2013.01); *A61F 2/966* (2013.01); *A61B 2017/12054* (2013.01); *A61F 2002/9511* (2013.01)

(58) Field of Classification Search
CPC .. A61B 2017/1205; A61B 2017/12054; A61B 2017/12095; A61F 2/011
See application file for complete search history.

(56) References Cited

U.S. PATENT DOCUMENTS 2,220,203 A 11/1940 Branin
3,429,408 A 2/1969 Maker et al.
4,858,810 A 8/1989 Intlekofer et al.
5,069,674 A 12/1991 Fearnot et al.
5,108,407 A 4/1992 Geremia et al.
5,122,136 A 6/1992 Guglielmi et al.
(Continued)

FOREIGN PATENT DOCUMENTS

CN 102125451 A 7/2011
CN 103356260 A 10/2013
(Continued)

OTHER PUBLICATIONS

International Search Report and Written Opinion issued in International Patent Application No. PCT/IB2023/051223 dated Apr. 26, 2023.

*Primary Examiner* — Ryan J. Severson
*Assistant Examiner* — Zehra Jaffri
(74) *Attorney, Agent, or Firm* — Troutman Pepper Locke LLP

(57) ABSTRACT

Various systems and methods of deploying an implantable medical device to a target location of a body vessel are disclosed. A delivery system can include a tubular body defining a longitudinal axis. The tubular body can include a lumen extending therethrough, a sidewall surrounding the lumen, and a feature formed from the sidewall. The feature can include an aperture. A pull wire can be extended through the lumen. The delivery system can include an implantable medical device that includes a locking portion. The locking portion can include an opening. The feature can be positioned within the opening of the locking portion. A distal end of the pull wire can pass through the aperture of the feature to secure the implantable medical device to the delivery system.

20 Claims, 4 Drawing Sheets

(56) References Cited

U.S. PATENT DOCUMENTS

D329,698 S 9/1992 Loney et al.
5,234,437 A 8/1993 Sepetka
5,250,071 A 10/1993 Palermo
5,263,964 A 11/1993 Purdy
5,334,210 A 8/1994 Gianturco
5,350,397 A 9/1994 Palermo et al.
5,382,259 A 1/1995 Phelps et al.
5,392,791 A 2/1995 Nyman
5,484,409 A 1/1996 Atkinson et al.
5,536,248 A 7/1996 Weaver et al.
5,569,221 A 10/1996 Houser et al.
5,645,558 A 7/1997 Horton
5,899,935 A 5/1999 Ding
5,925,059 A 7/1999 Palermo et al.
6,113,622 A 9/2000 Hieshima
6,203,547 B1 3/2001 Nguyen et al.
6,391,037 B1 5/2002 Greenhalgh
6,454,780 B1 9/2002 Wallace
6,506,204 B2 1/2003 Mazzocchi
6,561,988 B1 5/2003 Turturro et al.
7,367,987 B2 5/2008 Balgobin et al.
7,371,251 B2 5/2008 Mitelberg et al.
7,371,252 B2 5/2008 Balgobin et al.
7,377,932 B2 5/2008 Mitelberg et al.
7,384,407 B2 6/2008 Rodriguez et al.
7,708,754 B2 5/2010 Balgobin et al.
7,708,755 B2 5/2010 Davis, III et al.
7,799,052 B2 9/2010 Balgobin et al.
7,811,305 B2 10/2010 Balgobin et al.
7,819,891 B2 10/2010 Balgobin et al.
7,819,892 B2 10/2010 Balgobin et al.
7,901,444 B2 3/2011 Slazas
7,985,238 B2 7/2011 Balgobin et al.
8,062,325 B2 11/2011 Mitelberg et al.
8,333,796 B2 12/2012 Tompkins et al.
8,926,650 B2 1/2015 Que et al.
8,956,381 B2 2/2015 Que et al.
9,155,540 B2 10/2015 Lorenzo
9,232,992 B2 1/2016 Heidner
9,314,326 B2 4/2016 Wallace et al.
9,532,792 B2 1/2017 Galdonik et al.
9,532,873 B2 1/2017 Kelley
9,533,344 B2 1/2017 Monetti et al.
9,539,011 B2 1/2017 Chen et al.
9,539,022 B2 1/2017 Bowman
9,539,122 B2 1/2017 Burke et al.
9,539,382 B2 1/2017 Nelson
9,549,830 B2 1/2017 Bruszewski et al.
9,554,805 B2 1/2017 Tompkins et al.
9,561,125 B2 2/2017 Bowman et al.
9,572,982 B2 2/2017 Burnes et al.
9,579,484 B2 2/2017 Barnell
9,585,642 B2 3/2017 Dinsmoor et al.
9,615,832 B2 4/2017 Bose et al.
9,615,951 B2 4/2017 Bennett et al.
9,622,753 B2 4/2017 Cox
9,636,115 B2 5/2017 Henry et al.
9,636,439 B2 5/2017 Chu et al.
9,642,675 B2 5/2017 Werneth et al.
9,655,633 B2 5/2017 Leynov et al.
9,655,645 B2 5/2017 Staunton
9,655,989 B2 5/2017 Cruise et al.
9,662,120 B2 5/2017 Lagodzki et al.
9,662,129 B2 5/2017 Galdonik et al.
9,662,238 B2 5/2017 Dwork et al.
9,662,425 B2 5/2017 Lilja et al.
9,668,898 B2 6/2017 Wong
9,675,477 B2 6/2017 Thompson
9,675,782 B2 6/2017 Connolly
9,676,022 B2 6/2017 Ensign et al.
9,692,557 B2 6/2017 Murphy
9,693,852 B2 7/2017 Lam et al.
9,700,262 B2 7/2017 Janik et al.
9,700,399 B2 7/2017 Acosta-Acevedo
9,717,421 B2 8/2017 Griswold et al.
9,717,500 B2 8/2017 Tieu et al.
9,717,502 B2 8/2017 Teoh et al.
9,724,103 B2 8/2017 Cruise et al.
9,724,526 B2 8/2017 Strother et al.
9,750,565 B2 9/2017 Bloom et al.
9,757,260 B2 9/2017 Greenan
9,764,111 B2 9/2017 Gulachenski
9,770,251 B2 9/2017 Bowman et al.
9,770,577 B2 9/2017 Li et al.
9,775,621 B2 10/2017 Tompkins et al.
9,775,706 B2 10/2017 Peterson et al.
9,775,732 B2 10/2017 Khenansho
9,788,800 B2 10/2017 Mayoras, Jr.
9,795,391 B2 10/2017 Saatchi et al.
9,801,980 B2 10/2017 Karino et al.
9,808,599 B2 11/2017 Bowman et al.
9,833,252 B2 12/2017 Sepetka et al.
9,833,604 B2 12/2017 Lam et al.
9,833,625 B2 12/2017 Waldhauser et al.
9,918,718 B2 3/2018 Lorenzo
10,149,676 B2 12/2018 Mirigian et al.
10,285,710 B2 5/2019 Lorenzo et al.
10,292,851 B2 5/2019 Gorochow
10,420,563 B2 9/2019 Hebert et al.
10,517,604 B2 12/2019 Bowman et al.
10,668,258 B1 6/2020 Calhoun et al.
10,806,402 B2 10/2020 Cadieu et al.
10,806,461 B2 10/2020 Lorenzo
11,951,026 B2 4/2024 Clinger et al.
2001/0049519 A1 12/2001 Holman et al.
2002/0072705 A1 6/2002 Vrba et al.
2002/0165569 A1 11/2002 Ramzipoor et al.
2002/0183786 A1 12/2002 Girton
2003/0009208 A1 1/2003 Snyder et al.
2003/0093094 A1 5/2003 Diaz et al.
2003/0181942 A1 9/2003 Sutton et al.
2004/0034363 A1 2/2004 Wilson et al.
2004/0059367 A1 3/2004 Davis et al.
2004/0087964 A1 5/2004 Diaz et al.
2006/0025801 A1 2/2006 Lulo et al.
2006/0064151 A1 3/2006 Guterman
2006/0100687 A1 5/2006 Fahey et al.
2006/0116711 A1 6/2006 Elliott et al.
2006/0116714 A1 6/2006 Sepetka et al.
2006/0135986 A1 6/2006 Wallace et al.
2006/0206139 A1 9/2006 Tekulve
2006/0241685 A1 10/2006 Wilson et al.
2006/0247677 A1 11/2006 Cheng et al.
2006/0276824 A1 12/2006 Mitelberg et al.
2006/0276825 A1 12/2006 Mitelberg et al.
2006/0276826 A1 12/2006 Mitelberg et al.
2006/0276827 A1 12/2006 Mitelberg et al.
2006/0276830 A1 12/2006 Balgobin et al.
2006/0276832 A1* 12/2006 Balgobin ......... A61B 17/12154
606/200
2006/0276833 A1 12/2006 Balgobin et al.
2007/0010850 A1 1/2007 Balgobin et al.
2007/0055302 A1 3/2007 Henry et al.
2007/0083132 A1 4/2007 Sharrow
2007/0203519 A1 8/2007 Lorenzo et al.
2007/0233168 A1 10/2007 Davis et al.
2007/0270903 A1 11/2007 Davis, III et al.
2008/0027561 A1 1/2008 Mitelberg et al.
2008/0045997 A1 2/2008 Balgobin et al.
2008/0082176 A1* 4/2008 Slazas .............. A61B 17/12022
623/23.72
2008/0097462 A1 4/2008 Mitelberg et al.
2008/0119887 A1 5/2008 Que et al.
2008/0269719 A1 10/2008 Balgobin et al.
2008/0269721 A1 10/2008 Balgobin et al.
2008/0281350 A1 11/2008 Sepetka
2008/0300616 A1 12/2008 Que et al.
2008/0306503 A1 12/2008 Que et al.
2009/0062726 A1 3/2009 Ford et al.
2009/0099592 A1 4/2009 Buiser et al.
2009/0270877 A1* 10/2009 Johnson .................... A61F 2/95
606/108
2009/0312748 A1 12/2009 Johnson et al.
2010/0094395 A1 4/2010 Kellett

(56) References Cited

U.S. PATENT DOCUMENTS

| | | | |
|---|---|---|---|
| 2010/0114017 | A1 | 5/2010 | Lenker et al. |
| 2010/0174269 | A1* | 7/2010 | Tompkins ........ A61B 17/12022 604/507 |
| 2010/0206453 | A1 | 8/2010 | Leeflang et al. |
| 2010/0324649 | A1 | 12/2010 | Mattsson |
| 2011/0092997 | A1 | 4/2011 | Kang |
| 2011/0118772 | A1 | 5/2011 | Chen et al. |
| 2011/0118776 | A1 | 5/2011 | Chen et al. |
| 2011/0202085 | A1 | 8/2011 | Loganathan et al. |
| 2011/0295303 | A1 | 12/2011 | Freudenthal |
| 2012/0035707 | A1 | 2/2012 | Mitelberg et al. |
| 2012/0041472 | A1 | 2/2012 | Tan et al. |
| 2012/0083868 | A1 | 4/2012 | Shrivastava et al. |
| 2012/0172913 | A1 | 7/2012 | Kurrus et al. |
| 2012/0172921 | A1 | 7/2012 | Yamanaka et al. |
| 2012/0179194 | A1 | 7/2012 | Wilson et al. |
| 2012/0283768 | A1 | 11/2012 | Cox et al. |
| 2012/0289772 | A1 | 11/2012 | O'Connell et al. |
| 2013/0066413 | A1 | 3/2013 | Jin et al. |
| 2013/0296915 | A1 | 11/2013 | Bodewadt |
| 2013/0325054 | A1 | 12/2013 | Watson |
| 2013/0338678 | A1 | 12/2013 | Loushin et al. |
| 2014/0058435 | A1 | 2/2014 | Jones et al. |
| 2014/0088565 | A1 | 3/2014 | Vongphakdy et al. |
| 2014/0135812 | A1 | 5/2014 | Divino et al. |
| 2014/0200607 | A1 | 7/2014 | Sepetka et al. |
| 2014/0207175 | A1 | 7/2014 | Aggerholm |
| 2014/0243883 | A1 | 8/2014 | Tsukashima et al. |
| 2014/0277078 | A1 | 9/2014 | Slazas et al. |
| 2014/0277084 | A1 | 9/2014 | Mirigian et al. |
| 2014/0277085 | A1 | 9/2014 | Mirigian et al. |
| 2014/0277092 | A1 | 9/2014 | Teoh et al. |
| 2014/0277093 | A1 | 9/2014 | Guo et al. |
| 2014/0277100 | A1 | 9/2014 | Kang |
| 2015/0005808 | A1 | 1/2015 | Chouinard et al. |
| 2015/0025562 | A1 | 1/2015 | Dinh et al. |
| 2015/0119884 | A1 | 4/2015 | Fung et al. |
| 2015/0164666 | A1 | 6/2015 | Johnson et al. |
| 2015/0182227 | A1 | 7/2015 | Le et al. |
| 2015/0230802 | A1 | 8/2015 | Lagodzki et al. |
| 2015/0335333 | A1 | 11/2015 | Jones et al. |
| 2016/0008003 | A1 | 1/2016 | Kleshinski et al. |
| 2016/0022275 | A1 | 1/2016 | Garza |
| 2016/0022445 | A1 | 1/2016 | Ruvalacaba et al. |
| 2016/0045347 | A1 | 2/2016 | Smouse et al. |
| 2016/0157869 | A1 | 6/2016 | Elgård et al. |
| 2016/0228125 | A1 | 8/2016 | Pederson, Jr. et al. |
| 2016/0278782 | A1 | 9/2016 | Anderson et al. |
| 2016/0310304 | A1 | 10/2016 | Mialhe |
| 2016/0331383 | A1 | 11/2016 | Hebert et al. |
| 2016/0346508 | A1 | 12/2016 | Williams et al. |
| 2017/0007264 | A1 | 1/2017 | Cruise et al. |
| 2017/0007265 | A1 | 1/2017 | Guo et al. |
| 2017/0020670 | A1 | 1/2017 | Murray et al. |
| 2017/0020700 | A1 | 1/2017 | Bienvenu et al. |
| 2017/0027640 | A1 | 2/2017 | Kunis et al. |
| 2017/0027692 | A1 | 2/2017 | Bonhoeffer et al. |
| 2017/0027725 | A1 | 2/2017 | Argentine |
| 2017/0035436 | A1 | 2/2017 | Morita |
| 2017/0035567 | A1 | 2/2017 | Duffy |
| 2017/0042548 | A1 | 2/2017 | Lam |
| 2017/0049596 | A1 | 2/2017 | Schabert |
| 2017/0071737 | A1 | 3/2017 | Kelley |
| 2017/0072165 | A1 | 3/2017 | Lim et al. |
| 2017/0072452 | A1 | 3/2017 | Monetti et al. |
| 2017/0079671 | A1 | 3/2017 | Morero et al. |
| 2017/0079680 | A1 | 3/2017 | Bowman |
| 2017/0079766 | A1 | 3/2017 | Wang et al. |
| 2017/0079767 | A1 | 3/2017 | Leon-Yip |
| 2017/0079812 | A1 | 3/2017 | Lam et al. |
| 2017/0079817 | A1 | 3/2017 | Sepetka et al. |
| 2017/0079819 | A1 | 3/2017 | Pung et al. |
| 2017/0079820 | A1 | 3/2017 | Lam et al. |
| 2017/0086851 | A1 | 3/2017 | Wallace et al. |
| 2017/0086996 | A1 | 3/2017 | Peterson et al. |
| 2017/0095258 | A1 | 4/2017 | Tassoni et al. |
| 2017/0095259 | A1 | 4/2017 | Tompkins et al. |
| 2017/0100126 | A1 | 4/2017 | Bowman et al. |
| 2017/0100141 | A1 | 4/2017 | Morero et al. |
| 2017/0100143 | A1 | 4/2017 | Granfield |
| 2017/0100183 | A1 | 4/2017 | Iaizzo et al. |
| 2017/0105739 | A1 | 4/2017 | Dias et al. |
| 2017/0113023 | A1 | 4/2017 | Steingisser et al. |
| 2017/0147765 | A1 | 5/2017 | Mehta |
| 2017/0151032 | A1 | 6/2017 | Loisel |
| 2017/0165062 | A1 | 6/2017 | Rothstein |
| 2017/0165065 | A1 | 6/2017 | Rothstein et al. |
| 2017/0165454 | A1 | 6/2017 | Tuohy et al. |
| 2017/0172581 | A1 | 6/2017 | Bose et al. |
| 2017/0172766 | A1 | 6/2017 | Vong et al. |
| 2017/0172772 | A1 | 6/2017 | Khenansho |
| 2017/0189033 | A1 | 7/2017 | Sepetka et al. |
| 2017/0189035 | A1 | 7/2017 | Porter |
| 2017/0215902 | A1 | 8/2017 | Leynov et al. |
| 2017/0216484 | A1 | 8/2017 | Cruise et al. |
| 2017/0224350 | A1 | 8/2017 | Shimizu et al. |
| 2017/0224355 | A1 | 8/2017 | Bowman et al. |
| 2017/0224467 | A1 | 8/2017 | Piccagli et al. |
| 2017/0224511 | A1 | 8/2017 | Dwork et al. |
| 2017/0224953 | A1 | 8/2017 | Tran et al. |
| 2017/0231749 | A1 | 8/2017 | Perkins et al. |
| 2017/0245864 | A1 | 8/2017 | Franano et al. |
| 2017/0245885 | A1 | 8/2017 | Lenker |
| 2017/0252064 | A1 | 9/2017 | Staunton |
| 2017/0258476 | A1 | 9/2017 | Hayakawa et al. |
| 2017/0265983 | A1 | 9/2017 | Lam et al. |
| 2017/0281192 | A1 | 10/2017 | Tieu et al. |
| 2017/0281331 | A1 | 10/2017 | Perkins et al. |
| 2017/0281344 | A1 | 10/2017 | Costello |
| 2017/0281909 | A1 | 10/2017 | Northrop et al. |
| 2017/0281912 | A1 | 10/2017 | Melder et al. |
| 2017/0290593 | A1 | 10/2017 | Cruise et al. |
| 2017/0290654 | A1 | 10/2017 | Sethna |
| 2017/0296324 | A1 | 10/2017 | Argentine |
| 2017/0296325 | A1 | 10/2017 | Marrocco et al. |
| 2017/0303939 | A1 | 10/2017 | Greenhalgh et al. |
| 2017/0303942 | A1 | 10/2017 | Greenhalgh et al. |
| 2017/0303947 | A1 | 10/2017 | Greenhalgh et al. |
| 2017/0303948 | A1 | 10/2017 | Wallace et al. |
| 2017/0304041 | A1 | 10/2017 | Argentine |
| 2017/0304097 | A1 | 10/2017 | Corwin et al. |
| 2017/0304595 | A1 | 10/2017 | Nagasrinivasa et al. |
| 2017/0312109 | A1 | 11/2017 | Le |
| 2017/0312484 | A1 | 11/2017 | Shipley et al. |
| 2017/0316561 | A1 | 11/2017 | Helm et al. |
| 2017/0319826 | A1 | 11/2017 | Bowman et al. |
| 2017/0333228 | A1 | 11/2017 | Orth et al. |
| 2017/0333236 | A1 | 11/2017 | Greenan |
| 2017/0333678 | A1 | 11/2017 | Bowman et al. |
| 2017/0340383 | A1 | 11/2017 | Bloom et al. |
| 2017/0348014 | A1 | 12/2017 | Wallace et al. |
| 2017/0348514 | A1 | 12/2017 | Guyon et al. |
| 2017/0367712 | A1 | 12/2017 | Johnson et al. |
| 2018/0028779 | A1 | 2/2018 | von Oepen et al. |
| 2018/0036508 | A1 | 2/2018 | Ozasa et al. |
| 2018/0078263 | A1 | 3/2018 | Stoppenhagen et al. |
| 2018/0228493 | A1 | 8/2018 | Aguilar et al. |
| 2018/0250150 | A1 | 9/2018 | Majercak et al. |
| 2018/0280667 | A1 | 10/2018 | Keren |
| 2018/0289375 | A1* | 10/2018 | Hebert ............. A61B 17/12172 |
| 2018/0296222 | A1 | 10/2018 | Hebert et al. |
| 2018/0325706 | A1 | 11/2018 | Hebert et al. |
| 2019/0142565 | A1 | 5/2019 | Follmer et al. |
| 2019/0159784 | A1 | 5/2019 | Sananes et al. |
| 2019/0192162 | A1 | 6/2019 | Lorenzo et al. |
| 2019/0201688 | A1 | 7/2019 | Olson |
| 2019/0231566 | A1 | 8/2019 | Tassoni et al. |
| 2019/0255290 | A1 | 8/2019 | Snyder et al. |
| 2019/0314033 | A1 | 10/2019 | Mirigian et al. |
| 2019/0328398 | A1 | 10/2019 | Lorenzo |
| 2020/0015876 | A1 | 1/2020 | Chou et al. |
| 2020/0078024 | A1 | 3/2020 | Tekulve |
| 2020/0138448 | A1 | 5/2020 | Dasnurkar et al. |
| 2020/0147347 | A1 | 5/2020 | Cottone |

(56) References Cited

U.S. PATENT DOCUMENTS

| | | | |
|---|---|---|---|
| 2020/0187951 A1 | 6/2020 | Blumenstyk | |
| 2020/0229957 A1 | 7/2020 | Bardsley et al. | |
| 2020/0397444 A1 | 12/2020 | Montidoro et al. | |
| 2020/0406048 A1 | 12/2020 | Rentas Torres et al. | |
| 2021/0001082 A1 | 1/2021 | Lorenzo et al. | |
| 2021/0045759 A1 | 2/2021 | Merhi et al. | |
| 2021/0085498 A1 | 3/2021 | Nygaard et al. | |
| 2021/0186513 A1 | 6/2021 | Hoshino et al. | |
| 2021/0196281 A1 | 7/2021 | Blumenstyk et al. | |
| 2021/0213252 A1 | 7/2021 | Lorenzo et al. | |
| 2021/0220013 A1 | 7/2021 | Libarnes et al. | |
| 2021/0338248 A1 | 11/2021 | Lorenzo et al. | |
| 2021/0346002 A1 | 11/2021 | Lorenzo et al. | |
| 2021/0353299 A1 | 11/2021 | Hamel et al. | |

FOREIGN PATENT DOCUMENTS

| | | | |
|---|---|---|---|
| CN | 104203341 | A | 12/2014 |
| CN | 106456422 | A | 2/2017 |
| CN | 109770985 | A | 5/2019 |
| EP | 1985244 | A2 | 10/2008 |
| EP | 2498691 | | 9/2012 |
| EP | 3092956 | A1 | 11/2016 |
| EP | 3501427 | A1 | 6/2019 |
| EP | 3795097 | A1 | 3/2021 |
| EP | 3799803 | A1 | 4/2021 |
| EP | 3854321 | A1 | 7/2021 |
| EP | 1188414 | A1 | 3/2022 |
| EP | 4119065 | A1 | 1/2023 |
| JP | H10-507090 | A | 7/1998 |
| JP | 2006-334408 | A | 12/2006 |
| JP | 2006346350 | A | 12/2006 |
| JP | 2012-523943 | A | 10/2012 |
| JP | 2013-78584 | A | 5/2013 |
| JP | 2014-399 | A | 1/2014 |
| JP | 2016-179174 | A | 10/2016 |
| JP | 2017-529894 | A | 10/2017 |
| WO | WO 2007/070793 | A2 | 6/2007 |
| WO | 2008064209 | A1 | 5/2008 |
| WO | WO 2009/132045 | A2 | 10/2009 |
| WO | WO 2012/158152 | A1 | 11/2012 |
| WO | WO 2016/014985 | A1 | 1/2016 |
| WO | WO 2017/066386 | A1 | 4/2017 |
| WO | WO 2018/022186 | A1 | 2/2018 |
| WO | WO 2020/148768 | A1 | 7/2020 |

* cited by examiner 10
12
18
20
90
94
96
140
144
150
152
154
156
508
L
2B

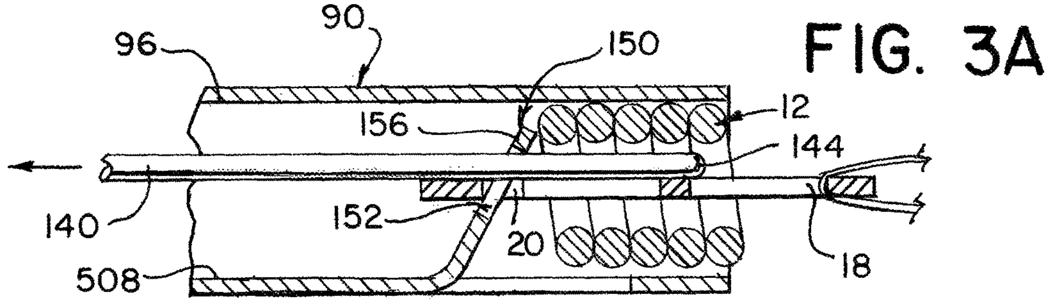
FIG. 3A
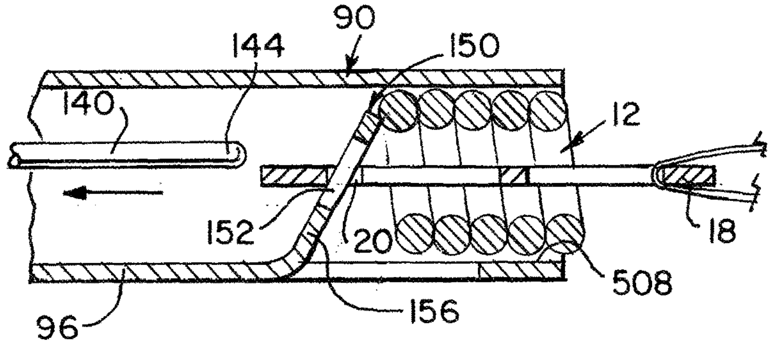
FIG. 3B
FIG. 3C
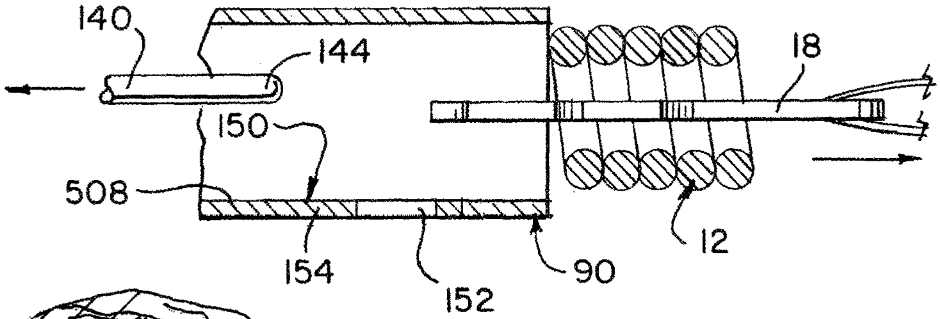
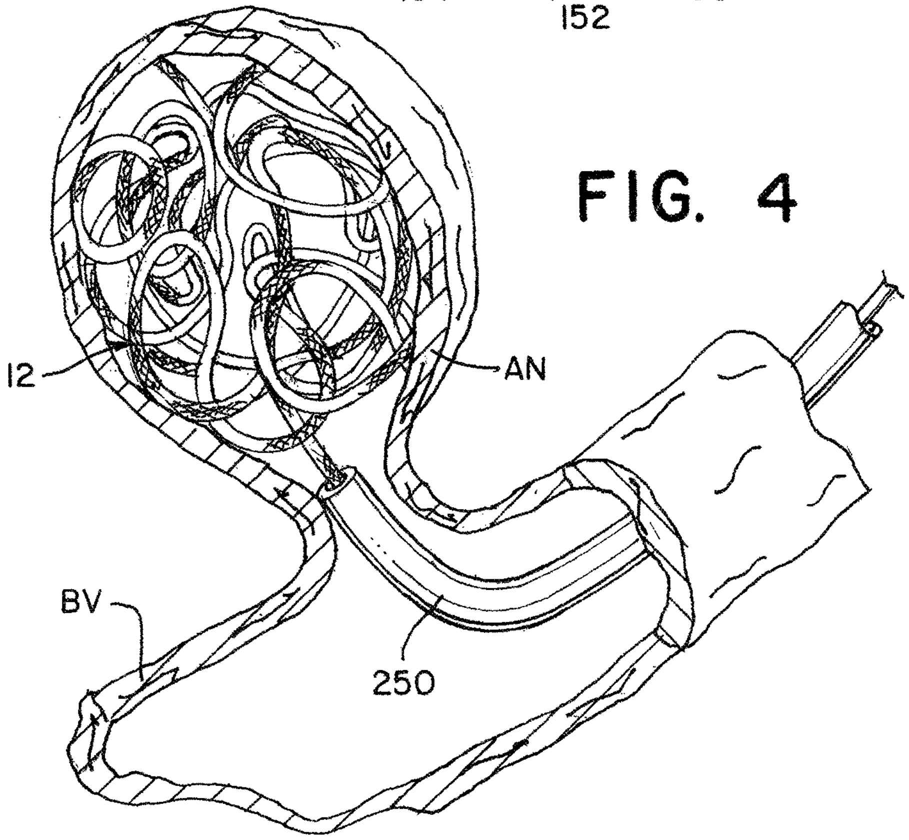
FIG. 4

FLEXIBLE FEATURE FOR EMBOLIC IMPLANT DEPLOYMENT

FIELD OF INVENTION

The present invention relate to aneurysm treatment devices and more particularly, to improved delivery systems for embolic implants.

BACKGROUND

Numerous intravascular implant devices are known in the field. Many are deployed mechanically, via systems that combine one or more catheters and wires for delivery. Examples of implants that can be delivered mechanically include embolic elements, stents, grafts, drug delivery implants, flow diverters, filters, stimulation leads, sensing leads, or other implantable structures delivered through a microcatheter. Some obstetric and gastrointestinal implants may also be implanted via similar systems that combine one or more catheters and wires. Devices that may be released or deployed by mechanical means vary greatly in design but can employ a similar delivery catheter and wire system. Many such catheter-based delivery systems include a wire for retention of the implant in the catheter until the time for release of the device. These systems are then actuated by retracting or pulling the wire relative to the catheter. Such a wire is referred to herein as a "pull wire". Many such catheter-based delivery systems also implement a "loop wire" having ends attached to the tubular body of the catheter and forming a loop through which the pull wire may be positioned in order to retain the implant in the catheter.

One issue with current catheter-based delivery systems is the complexity of attaching the loop wire to the tubular body of the catheter. The complexity of forming the loop wire and attaching the loop wire to the catheter delivery system lowers the reliability of the delivery system and increases the probability that the implant is prematurely detached from the catheter system.

Accordingly, there is a need for an improved implant delivery system that does not utilize a loop wire to retain the implant to the catheter system. This disclosure is directed to this and other considerations.

SUMMARY

Various systems and methods of deploying an implantable medical device to a target location of a body vessel are disclosed. A delivery system can include a tubular body defining a longitudinal axis. The tubular body can include a lumen extending therethrough, a sidewall surrounding the lumen, and a feature formed from the sidewall. The feature can include an aperture. A pull wire can be extended through the lumen. The delivery system can include an implantable medical device that includes a locking portion. The locking portion can include an opening. The feature can be positioned within the opening of the locking portion. A distal end of the pull wire can pass through the aperture of the feature to secure the implantable medical device to the delivery system.

In one aspect, a delivery system for deploying an implantable medical device to a target location of a body vessel is disclosed. The delivery system can include a tubular body that defines a longitudinal axis. The tubular body can include a lumen extending therethrough, a sidewall that surrounds the lumen, and a feature formed from the sidewall. The feature can include an aperture therethrough. The system can include a pull wire that extends through the lumen. The delivery system can include an implantable medical device, and the implantable medical device can include a locking portion that has an opening. The feature formed from the sidewall can be positioned within the opening of the locking portion of the implantable medical device. A distal end of the pull wire can pass through the aperture of the feature to secure the implantable medical device to the delivery system.

In some embodiments, the feature can include a tab shape that is cut into the sidewall and bent into a folded configuration. The feature can be deflected towards the longitudinal axis of the tubular body to secure the implantable medical device to the delivery system. In some embodiments, the feature can be laser cut from the sidewall.

In some embodiments, the feature can be configured to return to a non-folded configuration when the distal end of the pull wire is removed from the aperture, thereby deploying the implantable medical device to the target location of the body vessel.

In some embodiments, the feature is configured to impart an elastic force to the implantable medical device in response to the feature returning to the non-folded configuration from the folded-configuration.

In some embodiments, the feature can be formed of a memory-shape material.

In some embodiments, the pull wire can be coated with polytetrafluoroethylene (PTFE).

In some embodiments, the feature can be constructed of an elastic material.

In some embodiments, the distal end of the pull wire can be positioned through the aperture of the feature such that the distal end of the pull wire interferes with the locking portion which can secure the implantable medical device to the delivery system.

In some embodiments, when the pull wire is pulled proximally, the distal end of the pull wire is withdrawn from the aperture of the feature to release the implantable medical device from the delivery system.

In some embodiments, when the distal end of the pull wire is withdrawn from the aperture of the feature, the distal end of the pull wire no longer interferes with the locking portion, thereby facilitating release of the implantable medical device from the delivery system.

In another aspect, a method is disclosed. The method can include providing a tubular body that includes a lumen extending therethrough and a sidewall surrounding the lumen. The tubular body can define a longitudinal axis. The method can include forming a feature in the sidewall of the tubular body. The feature can include an aperture. The feature can be bent into a folded configuration from a non-folded configuration such that the feature is deflected towards a longitudinal axis of the tubular body. A pull wire can be extended through the lumen. A locking portion of an implantable medical device can be positioned over the feature in the folded configuration. A distal end of the pull wire can be positioned through the aperture of the feature to thereby secure the implantable medical device to the tubular body. The implantable medical device can be positioned approximate a target location of a body vessel. The pull wire can be translated proximally to thereby deploy the implantable medical device to the target location of the body vessel.

In some embodiments, the feature can include a tab shape cut into the sidewall and bent into a folded configuration. In some embodiments, forming the feature can include laser cutting the feature in the sidewall.

In some embodiments, deploying the implantable medical device to the target location of the body vessel can further include the feature returning to the non-folded configuration from the folded-configuration.

In some embodiments, the returning of the feature to the non-folded configuration can impart an elastic force to the implantable medical device as it is deployed to the target location of the body vessel.

In some embodiments, the method can include coating the pull wire with polytetrafluoroethylene (PTFE).

In some embodiments, when the pull wire is pulled proximally the distal end of the pull wire is withdrawn from the aperture of the feature to release the implantable medical device from the tubular body.

In some embodiments, when the distal end of the pull wire is withdrawn from the aperture of the feature, the distal end of the pull wire no longer interferes with the locking portion of the implantable medical device, thereby facilitating the release of the implantable medical device from the tubular body.

In some embodiments, the feature can be formed of a memory shape material.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 3A-3C illustrate a sequence of steps for releasing an implantable medical device from a feature of the delivery system, according to aspects of the present invention.

FIG. 4 is an illustration of an implantable medical device being positioned within an aneurysm according to aspects of the present invention.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figures 1, 2A, 2B, 2C, 2D:
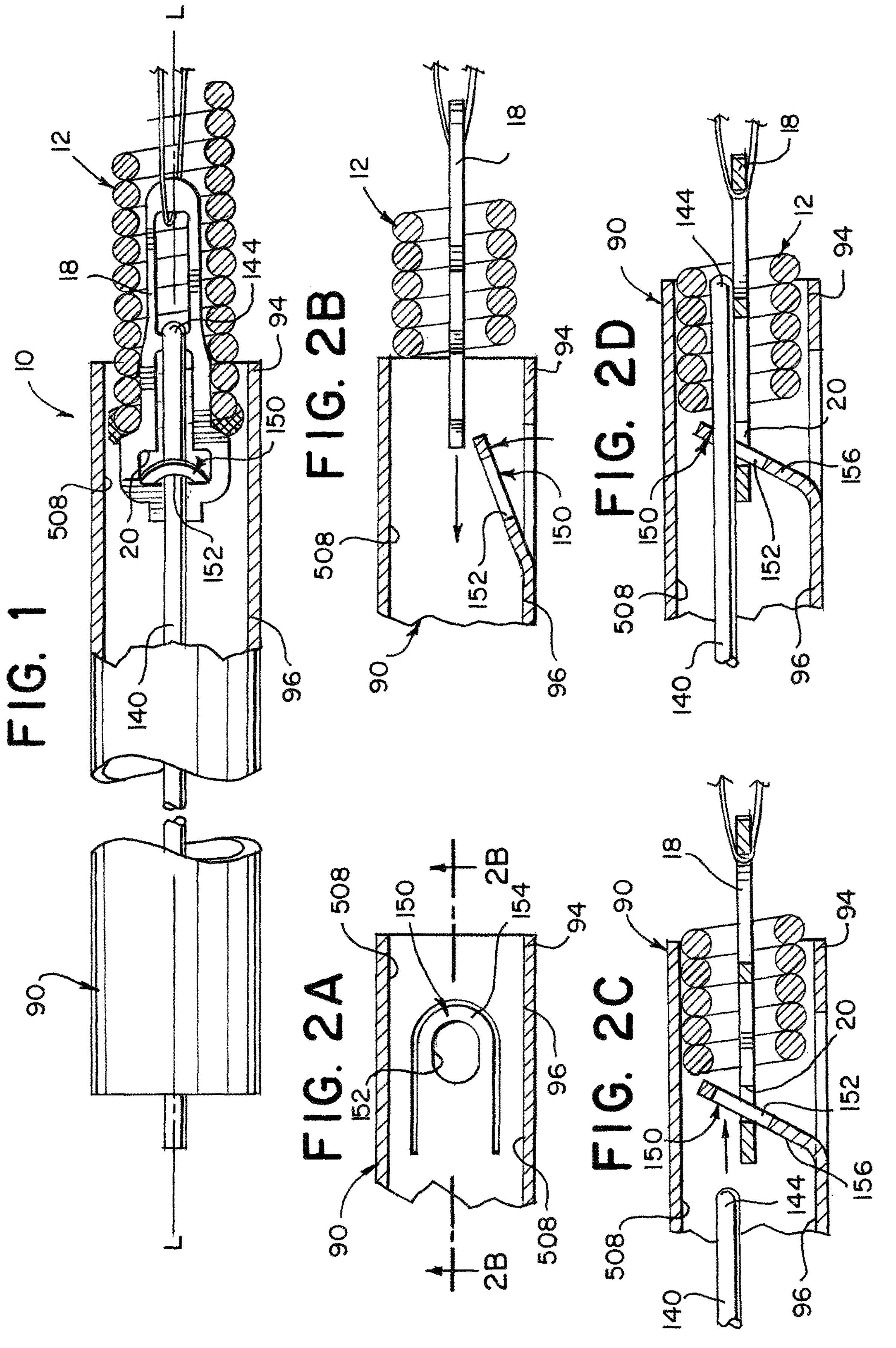
FIG. 1 an illustration of a delivery system and implant, according to aspects of the present invention.
FIGS. 2A-2D illustrate a sequence of steps for securing an implantable medical device to a feature of the delivery system, according to aspects of the present invention.

Turning to the figures, FIG. 1 shows an example delivery system 10 for deploying an implantable medical device 12 to a target location of a body vessel. The delivery system 10 can include a tubular body 90 that has a lumen 508 extending therethrough. The tubular body can define a longitudinal axis L-L. Lumen 508 can be surrounded by sidewall 96 of tubular body 90. Located approximate a distal end 94 of tubular body 90 can be a feature 150. Feature 150 can be formed from sidewall 96 of the tubular body 90. According to some embodiments, feature 150 can be a tab shape cut into the sidewall 96. According to some embodiments, the feature can be laser cut from the sidewall. The feature 150 can have a non-folded configuration at rest, and may automatically or resiliently returns to the non-folded configuration from a folded configuration, unless otherwise constrained. According to some embodiments, feature 150 can be constructed of an elastic material or a memory shape alloy, such as nitinol to allow the feature 150 to resiliently return from a folded-configuration to a non-folded configuration. As shown in FIG. 1, the feature 150 is in a folded-configuration and can be positioned through an opening 20 of a locking portion 18 of the implantable medical device 12. The folded configuration of the feature 150 can be characterized by the feature 150 being deflected towards the longitudinal axis L-L of the tubular body. According to some embodiments, the feature 150 can be constructed of a memory shape material, for example, such as nitinol. As shown, the implantable medical device 12 is located approximate the distal end 94 of the tubular body 90. A pull wire 140 can extend through the lumen 508 of the tubular body 90. A distal end 144 of the pull wire 140 can be positioned through an aperture 152 of the feature 10, after the feature 150 is positioned through the opening 20 of the locking portion 18. Once distal end 144 of the pull wire 140 is positioned through aperture 152 of feature 150, the implantable medical device 12 is secured to the delivery system 10. Pull wire 140 can be constructed out of any suitable material, for example, pull wire 140 can be constructed of stainless steel or memory shape material, such as nitinol. According to some embodiments, pull wire 140 can be coated with a polymer, such a polytetrafluoroethylene (PTFE).

FIGS. 2A-2D illustrate a sequence of steps for securing an implantable medical device to a feature of the delivery system, according to aspects of the present invention. FIG. 2A shows the feature 150 as it is shaped from sidewall 96 of the tubular body 90. The feature 150 can include an aperture 152. As shown in FIG. 2A, the feature 150 is in a non-folded configuration 154. FIG. 2B shows the feature 150 being folded towards longitudinal axis L-Land locking portion 18 of an implantable medical device 12 being positioned within lumen 508. FIG. 2C shows the feature 150 in the folded-configuration 156 now with locking portion 18 of an implantable medical device 12 (not shown) positioned over the feature 150. As shown, the locking portion 18 is positioned over feature 150 such that a portion of the feature 150 that includes the aperture 152 is positioned through the locking portion 18. In FIG. 2D, a distal end 144 of pull wire 140 is positioned through aperture 152 after the feature 150 is positioned through the locking portion 18 of the implantable medical device 12. In this configuration, the implantable medical device 12 is now secured to the delivery system 10.

FIGS. 3A-3C illustrate a sequence of steps for releasing an implantable medical device from a feature of the delivery system, according to aspects of the present invention. In FIG. 3A, the implantable medical device 12 (not shown) is secured to the delivery system 10 via the pull wire 140 interface with the feature 150 and the locking portion 18. In FIG. 3B, the distal end 144 of the pull wire 140 is withdrawn from aperture 152 of the feature 150. Feature 150 is now free to resiliently move from the folded configuration 156 to the non-folded configuration 154. FIG. 3C shows the moment after the distal end 144 of the pull wire 140 exits the aperture 152 of the feature 150. The arrow indicates that feature 150 resiliently moves from the folded configuration 156 to the non-folded configuration 154. The movement of feature 150 thereby allows the locking portion 18 of the implantable medical device to be detached from delivery system 10. In addition, the movement of feature 150 can impart an elastic force E that pushes the implantable medical device 18 towards a treatment site.

FIG. 4 is an illustration of embolic implant 12 being delivered through catheter 250 and positioned within an aneurysm A on a blood vessel BV. The implant can loop and bend with the aneurysm sac to form a thrombotic mass. The implant can loop back on themselves and/or loop next to other implants. As the aneurysm A becomes increasingly packed, overlapping portions of the implant 12 can press into each other.

Figures 5A, 5B, 5C, 5D:
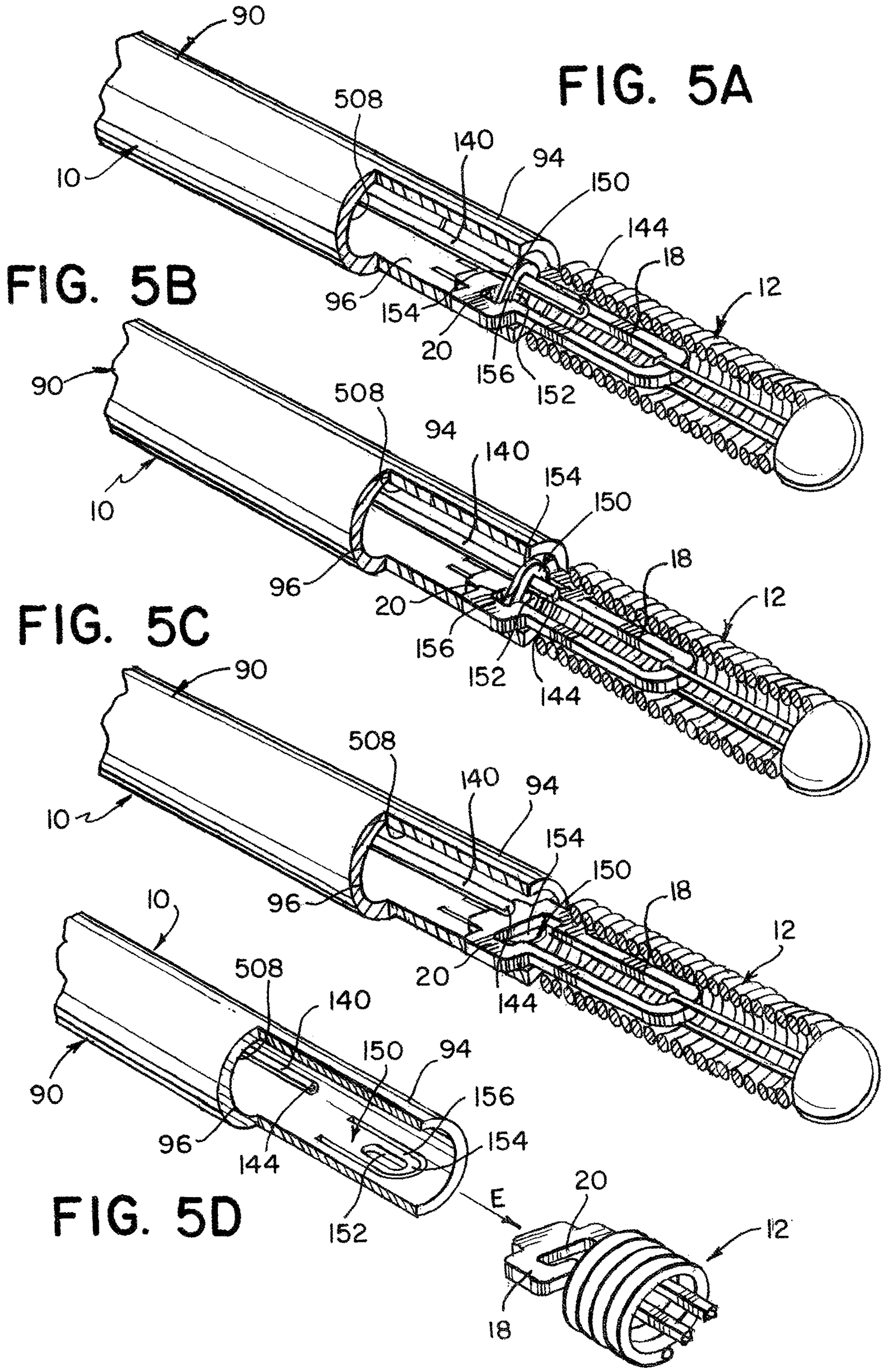
FIGS. 5A-5D illustrate a sequence of steps for releasing an implantable medical device from the delivery member, according to aspects of the present invention.

FIGS. 5A-5D illustrate a time sequence of steps for releasing an embolic implant 12 from a delivery system 10. The delivery system 10 can be configured such as illustrated in the previous figures and as otherwise described herein. FIG. 5A illustrates an engagement system including the feature 150 and pull wire 140 locked into a locking portion 18 of the medical device 12. The feature 150 can be in the folded configuration 156 and the feature can be positioned through an opening 20 of a locking portion 18 of the implantable medical device 12. When the distal end 144 of the pull wire 140 is put through the aperture 152 of the feature 150, the implantable medical device 12 is now secure. FIG. 5B illustrates the pull wire 140 being drawn proximally to begin the release sequence for the implantable medical device 12. FIG. 5C illustrates the instant the distal end 144 of the pull wire exits the aperture 152 and the pull wire 140 is pulled free of the feature 150. The feature 150 moves from the folded configuration 156 to the non-folded configuration 154 and exits the opening 20 of the locking portion 18. As can be seen, there is now nothing holding the medical device 12 to the delivery system 10. FIG. 5D illustrates the end of the release sequence. Here, the feature 150 has returned to the non-folded configuration 154 from the folded configuration 156. An elastic force E is imparted by the feature 150 to the implantable medical device 12 to "push" it away to ensure a clean separation and delivery of the implantable medical device 12.

Figure 6:
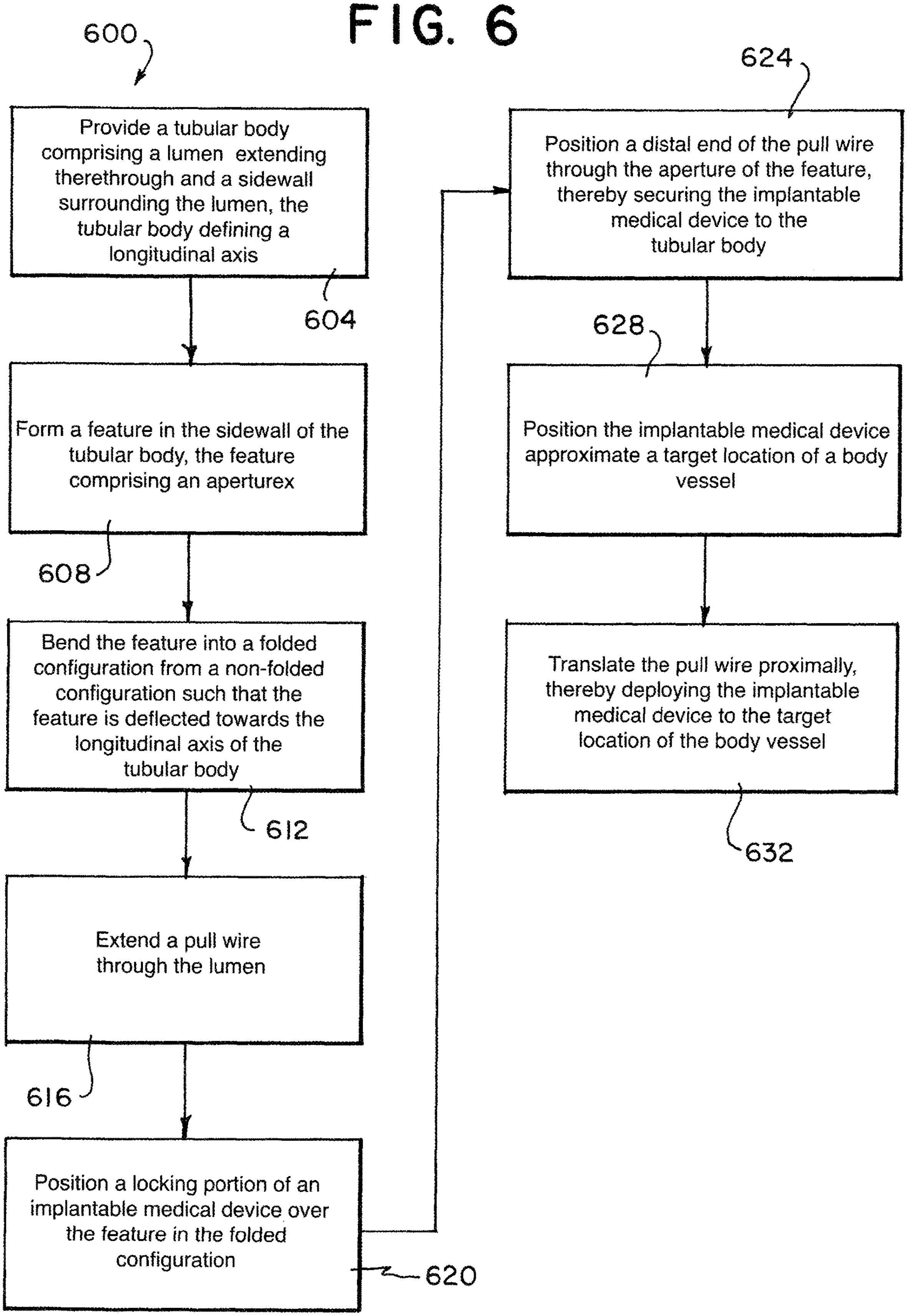
FIG. 6 is a flowchart of an example method of using the delivery system, according to aspects of the present invention.

FIG. 6 is a flowchart of an example method of using the delivery system, according to aspects of the present invention. In block 604, the method can include providing a tubular body 90. The tubular body 90 includes a lumen 508 that extends therethrough. The tubular body can define a longitudinal axis L-L. The lumen 508 can be surrounded by sidewall 96.

In block 608, the method can include forming a feature 150 in the sidewall 96 of the tubular body. The feature can include an aperture 152. In block 612, the method can include bending the feature 150 into a folded configuration 156 from a non-folded configuration 154. Once bent, the feature 150 can be deflected towards the longitudinal axis L-L of the tubular body 90.

In block 616, a pull wire 140 can be extended through the lumen 508. In block 620, the method can include positioning a locking portion 18 of an implantable medical device 12 over the feature 150 while the feature 150 is in the folded configuration 156. In block 624, the method can include positioning a distal end 144 of the pull wire 140 through the aperture 152 of the feature 150. Once the distal end 144 of the pull wire 140 is positioned through the aperture 152, the implantable medical device can be secured to the tubular body 90 of the delivery system 10.

In block 628, the method can include positioning the implantable medical device 12 approximate a target location of a body vessel. In block 632, the method can include translating the pull wire 140 proximally to thereby deploy the implantable medical device 12 to the target location of the body vessel.

In some embodiments, the feature can be formed as a tab shape cut into the sidewall 96 and bent into a folded configuration 156.

In some embodiments, forming the feature can further include laser cutting the feature 150 in the sidewall 96.

In some embodiments, deploying the implantable medical device 12 to the target location of the body vessel can further include the feature returning to the non-folded configuration 154 from the folded configuration 156.

In some embodiments, the return of the feature 150 to the non-folded configuration 154 can impart an elastic force (E) to the implantable medical device 12 as it is deployed to the target location of the body vessel.

In some embodiments, the method can include coating the pull wire 140 with PTFE.

In some embodiments, when the pull wire 140 is pulled proximally, the distal end 144 of the pull wire 140 is withdrawn from the aperture 152 of the feature to release the implantable medical device from the tubular body 90.

In some embodiments, when the distal end 144 of the pull wire 140 is withdrawn from the aperture 152 of the feature 150, the distal end 144 of the pull wire 140 no longer interferes with the locking portion 18 to thereby facilitate release of the implantable medical device from the tubular body 90. In some embodiments, the feature 150 can be formed of a memory shape material.

The descriptions contained herein are examples of embodiments of the invention and are not intended in any way to limit the scope of the invention. As described herein, the invention contemplates many variations and modifications of the implantation system and associated methods, including alternative geometries of system components, alternative materials, additional or alternative method steps, etc. Modifications apparent to those skilled in the pertinent art are intended to be within the scope of the claims which follow.

The invention claimed is:

1. A delivery system comprising:
- an implantable medical device releasably attached to the delivery system, the implantable medical device comprising at least one coil at a proximal end of the implantable medical device;
- a tubular body defining a longitudinal axis, the tubular body comprising:
  - a lumen extending therethrough; and
  - a sidewall surrounding the lumen; and
  - a feature cut from an inner surface of the sidewall and positioned proximally of a distal end of the tubular body, the feature comprising an aperture and directly contacting a proximal-most coil of the at least one coil;
  - a pull wire extending through the lumen; and
- a locking portion of the implantable medical device comprising an opening, the feature positioned within the opening of the locking portion such that a distal portion of the aperture of the feature extends upwards into the opening;
- wherein a distal end of the pull wire passes through the distal portion of the aperture of the feature to secure the implantable medical device to the delivery system, and
- wherein the feature is bent into a folded configuration and is releasably positioned within the opening of the locking portion such that proximal translation of a distal end of the pull wire causes the feature to resiliently return to a non-folded configuration approximately flush with the inner surface of the lumen.

2. The delivery system of claim 1, wherein the feature comprises a tab shape cut into the sidewall, and wherein the feature is deflected towards the longitudinal axis of the tubular body to secure the implantable medical device to the delivery system.

3. The delivery system of claim 1, wherein the feature is configured to return to the non-folded configuration, thereby deploying the implantable medical device to the target location of the body vessel.

4. The delivery system of claim 1, wherein the feature is configured to impart an elastic force to the implantable medical device in response to the feature returning to the non-folded configuration from the folded configuration.

5. The delivery system of claim 1, wherein the feature is formed of a memory shape material.

6. The delivery system of claim 1, wherein the pull wire is coated with polytetrafluoroethylene.

7. The delivery system of claim 1, the feature comprising an elastic material.

8. The delivery system of claim 1, wherein the distal end of the pull wire is positioned through the aperture of the feature such that the distal end of the pull wire interferes with the locking portion, thereby securing the implantable medical device to the delivery system.

9. The delivery system of claim 8, wherein when the pull wire is pulled proximally the distal end of the pull wire is withdrawn from the aperture of the feature to release the implantable medical device from the delivery system.

10. The delivery system of claim 9, wherein when the distal end of the pull wire is withdrawn from the aperture of the feature, the distal end of the pull wire no longer interferes with the locking portion, thereby facilitating release of the implantable medical device from the delivery system.

11. The delivery system of claim 1, wherein the return of the feature to the non-folded configuration pushes the implantable medical device toward the treatment site.

12. A method comprising: providing a tubular body comprising a lumen extending therethrough and a sidewall surrounding the lumen, the tubular body defining a longitudinal axis and further providing an implantable medical device comprising at least one coil at a proximal end of the implantable medical device;
- cutting a feature in an inner surface of the sidewall of the tubular body, the feature positioned proximally of a distal end of the tubular body and comprising an aperture;
- bending the feature into a folded configuration from a non-folded configuration such that the feature is deflected towards the longitudinal axis of the tubular body and directly contacts a proximal-most coil of the at least one coil at the proximal end of the implantable medical device;
- extending a pull wire through the lumen;
- positioning a locking portion of the implantable medical device over the feature in the folded configuration such that a distal portion of the aperture of the feature extends upwards into an opening of the locking device;
- positioning a distal end of the pull wire through the distal portion of the aperture of the feature, such that the distal end of the pull wire interferes with the locking portion, thereby securing the implantable medical device to the tubular body;
- positioning the implantable medical device approximate a target location of a body vessel; and
- translating the pull wire proximally, thereby deploying the implantable medical device to the target location of the body vessel,
- wherein the feature is releasably positioned within the opening of the locking portion such that the proximal translation of a distal end of the pull wire causes the feature to resiliently return to the non-folded configuration approximately flush with the inner surface of the lumen.

13. The method of claim 12, wherein the feature comprises a tab shape cut into the inner surface of the sidewall and bent into a folded configuration.

14. The method of claim 12, wherein deploying the implantable medical device to the target location of the body vessel further comprises the feature returning to the non-folded configuration.

15. The method of claim 14, wherein the returning of the feature to the non-folded configuration imparts an elastic force to the implantable medical device as it is deployed to the target location of the body vessel.

16. The method of claim 12, further comprising coating the pull wire with polytetrafluoroethylene.

17. The method of claim 12, wherein when the pull wire is pulled proximally the distal end of the pull wire is withdrawn from the aperture of the feature to release the implantable medical device from the tubular body.

18. The method of claim 17, wherein when the distal end of the pull wire is withdrawn from the aperture of the feature, the distal end of the pull wire no longer interferes with the locking portion, thereby facilitating release of the implantable medical device from the tubular body.

19. The method of claim 12, wherein the feature is formed of a memory shape material.

20. The method of claim 14, wherein the step of the feature returning to the non-folded configuration pushes the tubular body toward the treatment site.

* * * * *